United States Patent [19]

Roedel et al.

[11] Patent Number: 5,585,920
[45] Date of Patent: Dec. 17, 1996

[54] DEVICE FOR GENERATING A MAGNETIC FIELD IN AN ATOMIC ABSORPTION SPECTROMETER

[75] Inventors: Gunther Roedel, Owingen; Klaus P. Rogasch, Uhldingen-Muhlhofen, both of Germany

[73] Assignee: Bodenseewerk Perkin-Elmer GmbH, Uberlingen, Germany

[21] Appl. No.: 445,606

[22] PCT Filed: Apr. 3, 1989

[86] PCT No.: PCT/EP89/00355

§ 371 Date: Feb. 10, 1994

§ 102(e) Date: Feb. 10, 1994

[87] PCT Pub. No.: WO89/10025

PCT Pub. Date: Oct. 19, 1989

[30] Foreign Application Priority Data

Apr. 6, 1988 [DE] Germany ............... 38 11 446

[51] Int. Cl.$^6$ ..................... G01T 3/42
[52] U.S. Cl. ..................... 356/307
[58] Field of Search ............. 356/307, 312, 356/315; 361/160, 152, 206

[56] References Cited

U.S. PATENT DOCUMENTS

| | | | |
|---|---|---|---|
| 3,676,004 | 7/1972 | Prugger et al. | |
| 4,204,240 | 5/1980 | Schmoock | 361/152 |
| 4,341,470 | 7/1982 | Parker et al. | 356/307 |
| 4,365,288 | 12/1982 | Robe et al. | 363/141 |
| 4,632,549 | 12/1986 | Czabaffy et al. | 356/300 |

FOREIGN PATENT DOCUMENTS

| | | |
|---|---|---|
| 2256521 | 5/1973 | Germany . |
| 2452077 | 5/1976 | Germany . |

OTHER PUBLICATIONS

Smith, "DC Supplies from AC Sources", Wireless World, vol. 90, No. 1583, Sep. 1989, pp. 25–29.

Keuter et al, "Schaltugen . . . Bavelementen", Elektrotechnische Zeitschrift, E.T.Z., vol. 107, No. 5, pp. 200–202, 204, 206, 207.

*Primary Examiner*—K. Hantis
*Attorney, Agent, or Firm*—Edwin T. Grimes; David Aker

[57] ABSTRACT

An Atomic Absorption Spectrometer in which background absorption is compensated by means of a magnetic field causing a periodic line shift due to the Zeeman Effect, including a line emitting light source, an atomizing device, an optical system, by means of which the measuring light beam can be passed through an atom cloud of the atomizing device, an electromagnet, a converter circuit for converting the mains a.c. voltage into d.c. voltage applied to a capacitor, the winding of the electromagnet being located in the diagonal of a bridge circuit which is supplied with the d.c. voltage of the circuit and comprises a diode in diametrically opposite branches and a first and second controlled switch in the other two branches, the first one of the controlled switches being periodically maintained conductive by controls at the frequency of energizing and de-energizing the electromagnet, during an active time period encompassing the build-up and maintenance of the magnetic field, the first controlled switch being non-conductive during the remaining time, the second one of the controlled switches being controlled by means of a two-step current controller for regulating a predetermined current flowing through the winding of the electromagnet during the active time period of the first controlled switch, the second controlled switch likewise being non-conductive during the remaining time so that there results an essentially trapezoidal current waveform, and the winding of the electromagnet being connected in series with the diodes to the capacitor of the converter circuit in the non-conductive state of both of the controlled switches.

3 Claims, 4 Drawing Sheets

DEVICE FOR GENERATING A MAGNETIC FIELD IN AN ATOMIC ABSORPTION SPECTROMETER

TECHNICAL FIELD

The invention relates to a device for generating a magnetic field by means of an electromagnet arranged to be periodically switched on and off in order to cause a Zeeman effect for the compensation of the background absorption in an atomic absorption spectrometer Atomic absorption spectrometers serve to determine the amount or concentration of an element looked for in a sample. For this purpose a measuring light beam from a line emitting light source, a hollow cathode lamp for example, is directed to a photoelectric detector. An atomizing device is arranged in the path of the rays of this measuring light beam. The sample which is to be analyzed is atomized in this atomizing device such that the components of the sample are present in an atomic state. The measuring light beam contains the resonant lines of the element looked for. These resonant lines of the measuring light beam are absorbed by the atoms of the element looked for in the cloud of atoms, while, ideally, the other elements contained in the sample do not influence the measuring light beam. Therefore, the measuring light beam is subjected to an attenuation which is a measure of the number of the atoms looked for in the path of the measuring light beam and thus a measure of the concentration or the amount of the looked for element in the sample, depending on the method of atomization applied. The absorption to which the measuring light beam is subjected is not only caused by the atoms of the element looked for. There is a "background absorption" due to the absorption of the light by molecules, for example. This background absorption has to be compensated for with particularly highly sensitive measurements.

A flame may serve as an atomizing device into which a sample is sprayed as a solution. For highly sensitive measurements the electrothermal atomization is preferably used: The sample is introduced into a furnace which is heated to a high temperature by passing electrical current therethrough. Thereby, the sample is first dried then ashed, and lastly atomized. Then a "cloud of atoms" is generated in the furnace in which cloud the atom looked for is present in an atomic state. The measuring light beam is passed through this furnace. These furnaces can have different shapes. They are conventionally made of graphite.

The Zeeman effect is used for background compensation. When a magnetic field is applied to the absorbing atoms in the atomized sample, splitting and shifting of the resonant lines of these atoms is effected. Then the resonant lines of the atoms no longer coincide with the spectral lines of the measuring light beam and no atomic absorption takes place in the borderline case. This permits discrimination between non-atomic background absorption which is also present when the magnetic field is applied, and real atomic absorption which is superimposed onto the background absorption when the magnetic field is not applied.

This requires that an electromagnet in an atomic absorption spectrometer is alternately switched on and off in order to be able to measure the atomic absorption with the Zeeman effect and without the Zeeman effect. The invention relates to a device which achieves this.

BACKGROUND ART

From German patent application 1,964,469 (U.S. Pat. No. 3,676,004) an atomic absorption spectrometer is known wherein the radiation originates from a single light source designed as a line emitter, the radiation of which passing through the sample is frequency modulated by use of the longitudinal Zeeman effect. In this prior atomic absorption spectrometer a hollow cathode lamp is arranged between the pole pieces of an electromagnet. One of the pole pieces has a bore through which the measuring light beam passes. Then the measuring light beam is directed through a flame serving as an atomizing device and a monochromator and impinges upon a photoelectric detector. The electromagnet is arranged to be switched on and off, whereby the atomic absorption of the sample atoms compensated for with respect to the background absorption can be determined from the difference between the signals with the electromagnet switched off and switched on. The windings of the electromagnet are provided on the pole pieces.

In this prior art atomic absorption spectrometer the emission lines of the line emitting light source are periodically shifted by the Zeeman effect and thus the emitted light frequency is modulated and not the absorption lines of the sample. This may cause problems when a hollow cathode lamp is used as a light source because the discharge of the hollow cathode lamp is influenced by the magnetic field, as already mentioned in German Patent Application 1,964,469, From German patent application 2,165,106 it is known to apply the magnetic field of an electromagnet arranged to be switched on and off to the atomizing device, i.e. to the sample which is to be atomized, instead of to the light source. Therein the atomizing device is a flame. The magnetic field is applied perpendicular to the direction of the propagation of the measuring light beam. A splitting of the absorption lines due to the "transverse" Zeeman effect is effected, which again causes a relative shift of the emission lines of the measuring light beam and the absorption lines of the sample. Again, it is possible to discriminate between atomic absorption by the atoms of the element looked for and non-specific background absorption by switching the magnetic field on and off.

When the transverse Zeeman effect is used, a spectral line is split into a central line, the wave length of which corresponds to the non-shifted wave length of the respective line with the magnetic field switched off and two side lines which relative thereto are shifted to longer and shorter wave lengths. The central line and the side lines are polarized differently. Therefore, the influence of the central line can be eliminated by a polarizer.

In the prior art atomic absorption spectrometer a magnetic field causing the Zeeman effect is generated by an electromagnet which is excited by one-way rectified mains A.C. voltage. A narrow area of the half wave of the mains A.C. voltage around the maximum of the half wave is used for measuring the background absorption when the Zeeman effect occurs. Thereby, a relatively short useful signal results for the measurement of the background absorption. This useful signal is very much influenced by the mains frequency and the amplitude of the mains voltage.

A very strong magnetic field is required for splitting the spectral lines by the Zeeman effect which ensures a clear separation of emission lines and absorption lines. To achieve this a strong exciting current has to be generated in the winding of the electromagnet. In the prior art atomic absorption spectrometers this current is generated from the mains voltage. The power requirement of the electromagnet which causes the Zeeman effect in the prior art atomic absorption spectrometers is quite high. This causes, among others, an undesired heating up.

DISCLOSURE OF THE INVENTION

Finally it is an object of the invention to reduce the power consumption of the electromagnet and thus, also, the power loss compared to prior arrangments.

According to the invention this object is achieved by (a) means for transforming the mains A.C. voltage into a D.C. voltage on the input side (b) transformer means to which the D.C. voltage of the input side is supplied and which comprise inverter means for chopping the D.C. voltage of the input side with a frequency which is substantially higher than the mains frequency a transformer for stepping down the D.C. voltage chopped by the inverter means, and rectifier and filter means for generating D.C. voltage on the output side, and (c) a switching device for periodically supplying the D.C. voltage of the output side to the electromagnet.

Thus the mains A.C. voltage does not feed the electromagnet directly. On the contrary, at first a d.c. voltage is generate d from the mains A.C. voltage. This d.c. voltage is chopped at high frequency compared to that of the mains A.C. voltage. This chopped voltage is stepped down by means of a transformer. The transformer can be substantially smaller, as if the mains A.C. voltage had to be transformed directly, be cause the frequency is higher.

The stepped down voltage is rectified again. Then this rectified voltage is suitably pulsed and is supplied to the winding of the electromagnet. The pulsed supply to the winding of the electromagnet can be achieved by available electronic components because of the stepped down voltage. The frequency of this supply is no longer subjected to the mains frequency. It is also not required to limit the measurement with the Zeeman effect to a narrow area around the maximum of a half-wave. On the contrary, more favorable signal waveforms of the magnetic field can be achieved.

Modifications of the invention are subject matter of the sub-claims.

PREFERRED EMBODIMENT OF THE INVENTION

Figure 1:
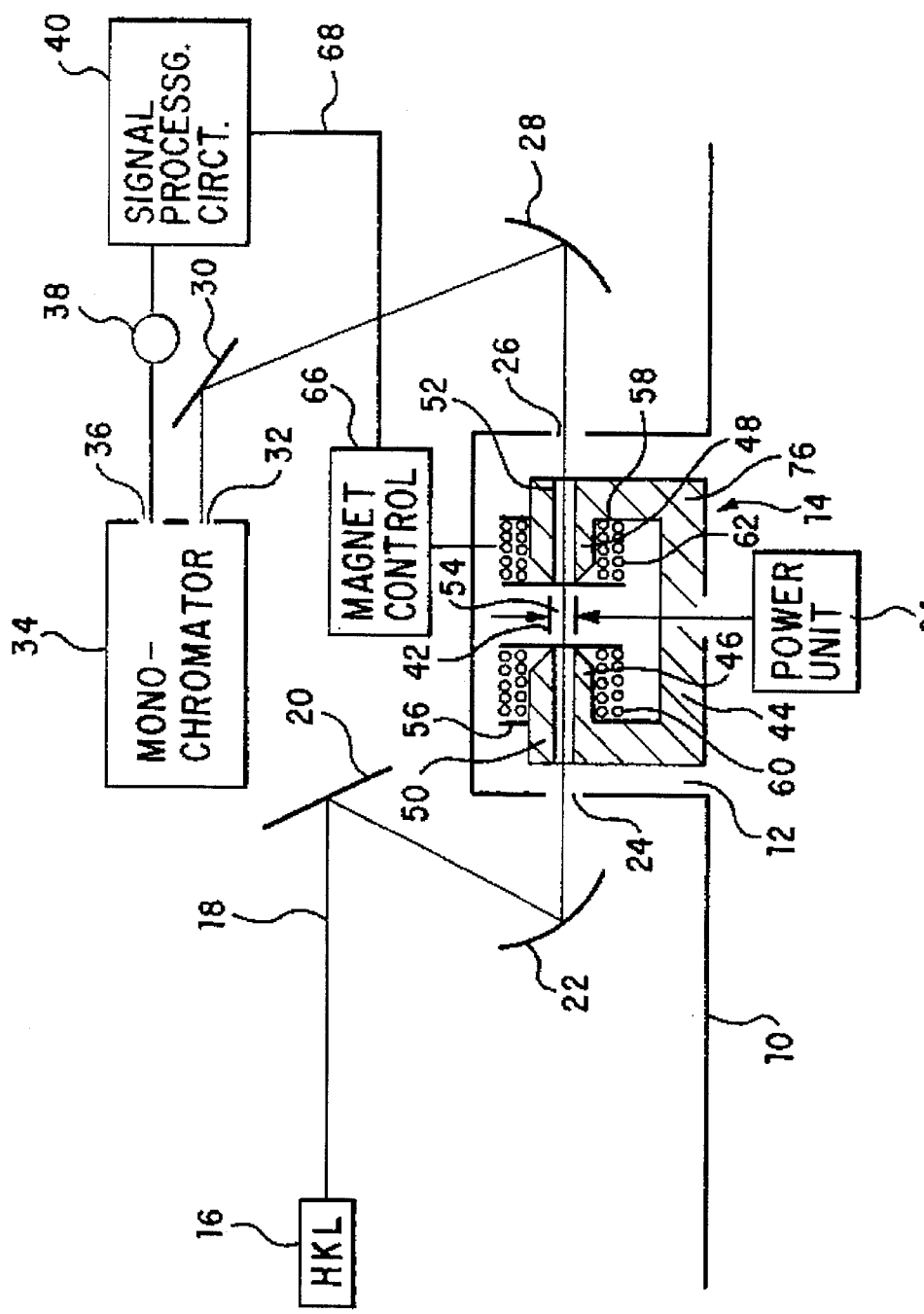
FIG. 1 schematically shows the construction of an atomic absorption spectrometer in which the background absorption is compensated for by the use of the longitudinal Zeeman effect.

FIG. 1 shows a schematical illustration of the entire atomic absorption spectrometer.

The atomic absorption spectrometer has a housing 10 in which the lamps, the optical system and the photosensitive detector are arranged. The housing defines a sample cavity 12. An atomizing device 14 is arranged in the sample cavity 12.

The atomic absorption spectrometer has a hollow cathode lamp as first light source 16. The light source 16 emits a line spectrum which corresponds to the resonant lines of a certain element looked for. A measuring light beam 18 originates from the light source 16. The measuring light beam 18 is deviated by a plane mirror 20 and collected in the center of the sample cavity by a concave mirror 22 through an opening 24 of the housing 10. Then the measuring light beam passes through an opening of the housing 10 aligned with the opening 24 and impinges upon a second concave mirror 28. The second concave mirror 28 focuses the measuring light beam 18 via a plane mirror 30 on the inlet slit 32 of a monochromator 34. A photoelectric detector 38 is arranged behind an outlet slit 36 of the monochromator 34. The signal of the photoelectric detector 38 is supplied to a signal processing circuit 40.

The atomizing device 14 comprises a furnace for electrothermal atomization, with only the actual furnace body of the furnace device being illustrated in FIG. 1, and an electromagnet 44 which is arranged to be switched on and off in order to generate a magnetic field at the location of the sample. The electromagnet 44 has two aligned pole pieces 44 and 46 between which the furnace body 42 is arranged. Aligned bores 50 and 52 are provided in the pole pieces 46 and 48. The bores 50 and 52 are aligned with a longitudinal bore 54 of the furnace body 42. The measuring light beam 18 passes through the bores 50 and 52 and through the longitudinal bore of the furnace body. Coil holders 56 and 58, respectevily, are arranged on the pole pieces 50 and 52. Coils 60 and 62, respectively, of the electromagnet 44 are wound around these coil holders 56 and 58. Numeral 64 designates a power unit which controls the current through the furnace body 42. As indicated the current is supplied transversely to the direction of the measuring light beam 18 and flows through the tubular furnace body 42 in a circumferential direction. The electromagnet 44 is controlled by a magnet control 66 such that the magnetic field is alternately switched on and off. At the location of the sample the magnetic field of the electromagnet 44 is directed within the furnace body in the direction of the propagation of the measuring light beam 18. Therefore, the longitudinal Zeeman effect is generated at the sample atoms when the magnetic field is switched on. That means that the absorption lines of the sample atoms are split into two lines, each of which is shifted relative to the undisturbed original absorption line. There is no atomic absorption in the sample with the wavelength of the original absorption line. Therefore also the atoms of the elements looked for do not absorb the measuring light beam 18 because this measuring light beam contains only the non-shifted resonant lines which are characteristic of the element. Therefore, only the background absorption is measured When the magnetic field is switched on. The portion of real atomic absorption corrected for the background absorption can be determined from the measurements with the magnetic field switched on and off. For this purpose the cycle of switching the electromagnet 44 on and off is supplied to the signal evaluation circuit 40 as indicated by a line 68. By using the longitudinal Zeeman effect a polarizer arranged in the path of rays can be omitted and the useful signal is improved.

Figure 2:
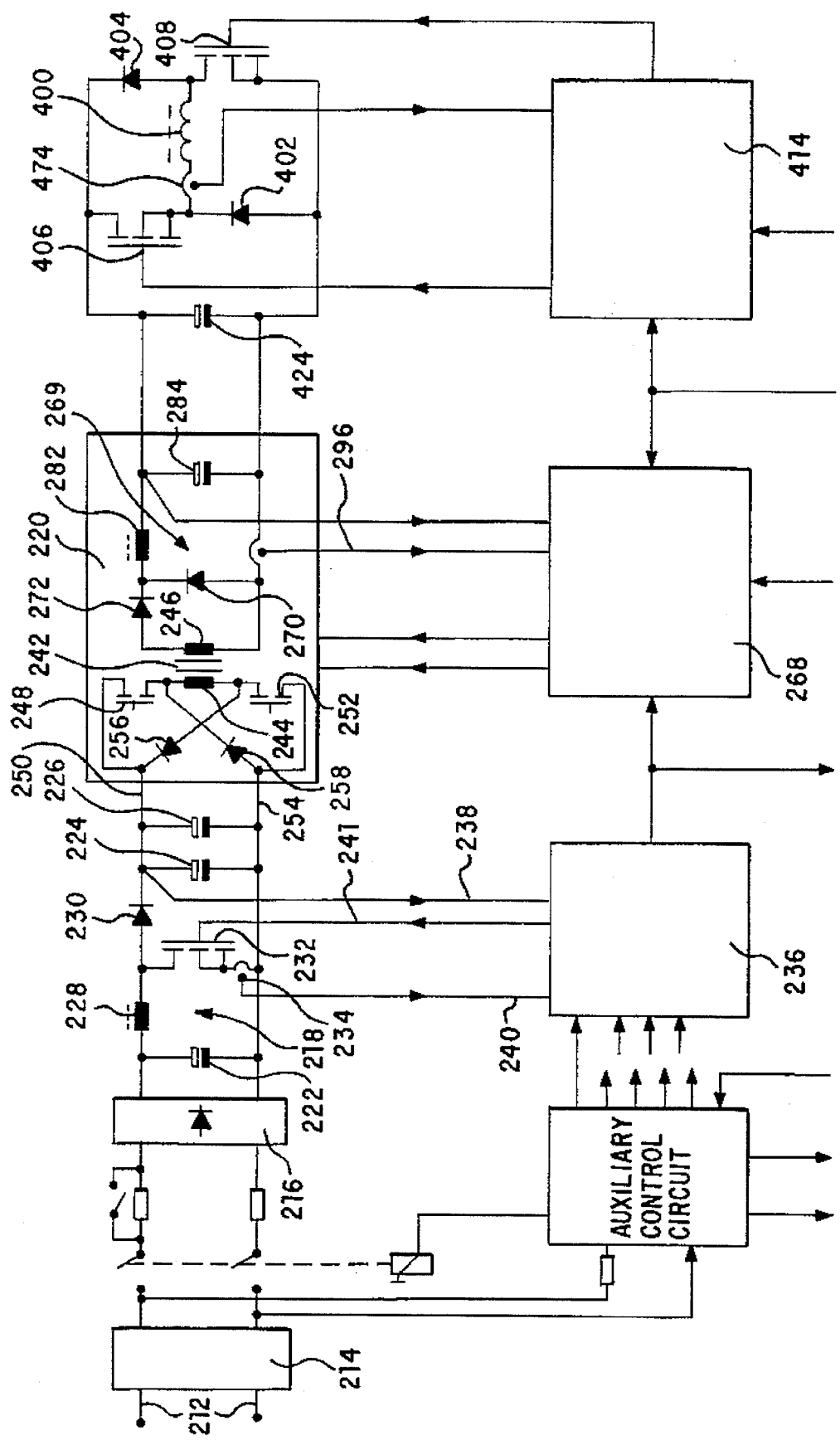
FIG. 2 shows a block diagram of the power unit for switching periodically the electromagnet on and off.

FIG. 2 shows a block diagram of the power unit 66 of FIG. 1.

The mains voltage is supplied to input terminals 212. It is passed through a filter 214 for noise suppressing and is rectified by a rectifier 216. The rectified mains voltage is supplied to a stepping-up converter 218 by which the rectified mains voltage is smoothed and a control led D.C. voltage is generated. Additionally, the stepping up converter ensures that a sinusoidal current is taken from the mains. The controlled D.C. voltage of the stepping up converter 218 forms the D.C. voltage of the input side of a convertor 220 connected to the output of the stepping up converter 218. This convertor will be described hereinbelow.

The stepping-up converter 218 comprises a capacitor 222 at the input and capacitors 224 and 226 connected in parallel at the output. Furthermore, the stepping up converter 218 comprises an inductor 228 and a diode 230. A transistor 232 connected to act as a controlled switch closes the electric circuit through the inductor 228. When the transistor 232 is inhibited the diode 230 is effective as a recovery diode through which the voltage induced in the inductor when the transistor 232 is inhibited charges the capacitors 224,226.

A current sensor 234 is arranged in series with the transistor 232. A controller 236 obtains the D.C. voltage supplied to the capacitors 224 and 226 through a line 238 and a signal from the current sensor through a line 240. The controller 236 controls the transistor 232 through a line 241.

The capacitors 224 and 226 provide the D.C. voltage for the input side of the convertor means 220.

The convertor means 220 comprise a transformer 242 with a primary winding 244 and a secondary winding 246. At a first end the primary winding 244 is connected to a positive input terminal 250 through a switching transistor 248. This input terminal is connected to corresponding terminals of the capacitors 224,226. At its second end the primary winding is connected to a negative input terminal 254 through a switching transistor 252. This input terminal is connected to the corresponding other terminals of the capacitors 224,226. The second end of the primary winding 244 is connected to the positive input terminal 250 through a diode 256. The passage direction of the diode 256 is from the second end of the primary winding 244 to the input terminal 250. The first end of the primary winding 244 is connected to the negative input terminal 254 through a diode 258. The conducting direction of the diode 258 is from the input terminal 254 to the first end of the primary winding 244.

The switching transistors 248 and 252 are periodically rendered conducting and non-conducting by a circuit 268 at a relatively high frequency compared to the mains frequency. The demagnetization current of the primary winding 244 can flow through the diodes 256,258.

A flux converter-rectifier circuit 269 with diodes 270,272 is connected to the secondary winding 246. The flux converter-rectifier circuit 269 provides a D.C. voltage. The D.C. voltage is smoothed by an inductor 282 and capacitors 284 connected parallelly. In this way a D.C. voltage is generated at output terminals 286 and 288. At the same At the same time, the capacitors 284 further energy accumulators.

Figure 3:
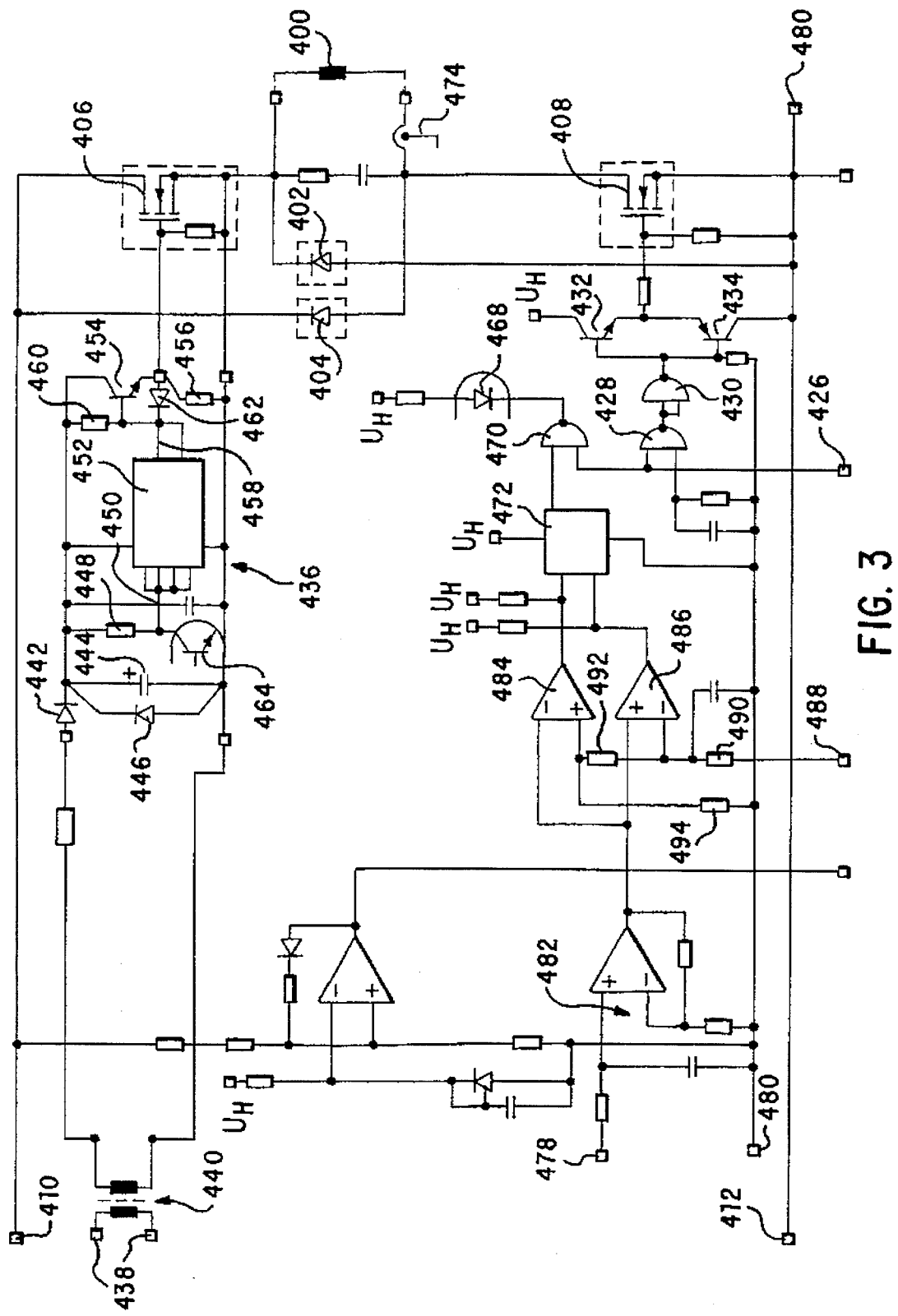
FIG. 3 shows the circuit for controlling the current through the the winding of the electromagnet in detail.

The switching transistors 248, 252 are controlled by the circuit 268 which is illustrated in detail in FIG. 3.

The winding 400 of the electromagnet 44 which is formed by the field coils 60 and 62 is arranged in a bridge circuit of two diodes 402 and 404 arranged in diametrically opposite branches of the bridge circuit and two control led switches 406 and 408. The output voltage of the convertor means 220 is supplied to the bridge circuit. The winding 400 of the electromagnet 44 is arranged in the diagonal of the bridge.

The controlled switch 406, the winding 400 with a first end connected to the switch 406 and a second end connected the the switch 408, and the controlled switch 408 are arranged in series between the output voltage of the convertor means 220 which is applied to the terminals 410 and 412. The controlled switches 406, 408 are formed by switching transistors. The second end of the winding 400 is connected to the positive terminal 410 through the diode 404. The conductive direction of the diode 404 is from the second end of the winding 400 to the terminal 410. The first end of the winding 400 is connected to the terminal 412 through the diode 402. The conductive direction of the diode 402 is from the terminal 412 to the first end of the winding 400.

The switches 406 and 408 are controlled by a control circuit 414. This circuit will be explained with reference to FIG. 4.

Figure 4:
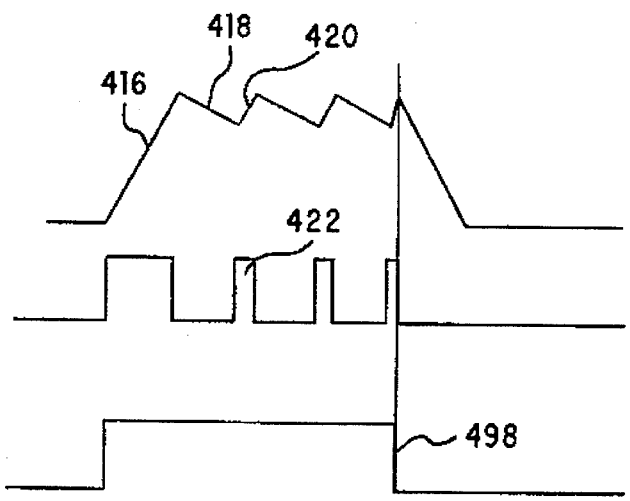
FIG. 4 shows the waveform of the current in the winding of the electromagnet and the switching conditions of the controlled switches in the circuit of FIG. 3.

During the de-energizing phase both switches 406 and 408 are open. In order to energize the electromagnet both switches 406 and 408 are closed. Due to the strong self-induction of the electromagnet 44 the current increases continuously with a finite inclination as illustrated by the flank 416. This increase continues until the desire d value of the current and thus that of the magnetic field is achieved. At this moment the switch 406 is opened. Thereby the magnetic field breaks down. The breaking down magnetic field induces a voltage in the winding 400 of the electromagnet 44, which voltage strives for maintaining the current flow existing hitherto. The winding 400 forms a voltage supply and generates a current flowing clockwise through the switch 408 and the diode 402 in FIG. 2. The current decreases slowly because of losses in this electric circuit, the decrease taking place more slowly than the increase as illustrated by numeral 418 in FIG. 4. When the current has decreased below a certain value the switch 406 is closed again. Then the current increases again with the inclination of the flank 416. This is illustrated in FIG. 4 by numeral 420. The desired value of the current is reached quickly. Therefore, the switch 406 is closed only for a short time as illustrated by the rectangular pulse 422. The control circuit 414 acts like a two-step current control with hysteresis by which the current through the winding 400 is maintained at a nearly constant level during the energizing phase.

When the electromagnet is to be de-energized again (FIG. 4, point 498), both switches 406 and 408 are open. At this time, the voltage induced by the breaking down magnetic field tries to maintain the current flow in the original direction. This current flow, however, takes place in the circuit comprising the diode 404, a capacitor 424 connected to the input of the bridge circuit, and the diode 402. In this way the capacitor 424 is charged again. The energy stored in the magnetic field of the electromagnet is again supplied to the capacitor 424. In this way the power requirement of the electromagnet for generating the magnetic field can be kept small. This also has a favorable effect on the design of the components. Also the heat caused by the electromagnet is reduced as compared to conventional arrangements.

The control circuit is illustrated in detail in FIG. 3. An energizing signal is supplied to an input 426 and initiates the energizing of the electromagnet 44. This energizing signal corresponds to the waveform of the signal in the lowermost line of FIG. 4. The switch 408 is closed, that means the switch transistor becomes conductive through inverters 428 and 430 and transistors 432 and 434. The switch 406 is controlled potential-freely by the driver stage 436. The driver stage 436 is energized through a transformer 440 by the mains voltage which is supplied to mains terminals 438. The output voltage of the transformer 440 is rectified by a diode 442 and charges a capacitor 444. The voltage supplied to the capacitor 444 is stabilized by a Zener diode 446. The positive voltage of the capacitor is supplied to the input 450 of an amplifier 452 through a resistor 448. The transitor 454 with an emitter resistor 456 is also connected to the voltage existing across the capacitor 444. The base of the transistor 454 is connected, on one hand, to the output 458 of the amplifier 452 and, on the other hand, through a resistor 460 to the positive terminal of the capacitor 444 operating as a D.C. voltage source. The emitter of the transistor 454 is connected to the output 458 of the amplifier 452 through a diode 462. Furthermore, the emitter of the transistor 454 is connected to the control electrode of the switch 406. A photo-transistor 464 which forms a part of an optical coupling device is connected to the negative terminal of the capacitor 444 at the input of the amplifier 452. The other part of the optical coupling device is a light-emitting diode 468 which is illustrated in the right lower quadrant of FIG. 3. When the light-emitting diode 468 does not emit, the photo-transistor 464 is non-conductive. The positive voltage of the capacitor is applied to the input 450 of the amplifier. Thereby, the output 458 of the amplifier becomes negative. The transistor 454 becomes non-conductive. The voltage at the control electrode of the switch 406 relative to the source becomes zero and the switch 406 becomes non-conductive. When, however, the light-emitting diode 468 emits, the photo-transistor 464 becomes conductive, the voltage at the input of the amplifier 452 becomes zero and the voltage at the output of the amplifier 452 becomes positive. The transistor 454 becomes conductive by the positive voltage at the output of the amplifier 452. Then the positive voltage is supplied to the control electrode of the switch 406 through the emitter-collector junction of the transistor 454. The switch becomes conductive.

The emission of the light-emitting diode depends on two conditions: Therefore, the light-emitting diode 468 is arranged between the D.C. supply voltage UH, which also represents the condition "H" (high) of the logical components, and the output of a NAND gate 470. The control signal of the input 426 is supplied to an input of the NAND gate 470. The output of a flipflop 472 is supplied to the other input of the NAND gate 470. The flipflop 472 forms part of a two-step current control with hysteresis for the current flowing in the winding 400 of the electromagnet 44. A signal representing the current flowing through the winding 400 is provided by a current sensor 474 with a Hall element. This signal is supplied to terminals 478,480 and is amplified by an amplifier 482. The output voltage of the amplifier 482 is supplied, on one hand, to the inverting input of a first comparator 484 and, on the other hand, to a non-inverting input of a second comparator 486. A voltage representing the desired value of the current flowing through the winding 400 is supplied to the input terminal 488. Two partial voltages are tapped from this voltage by means of a voltage divider consisting of three ohmic resistors 490, 492 and 494. The lower voltage is supplied to the non-inverting input of the comparator 484, the higher voltage is supplied to the inverting input of the compatator 486. Comparator 484 will change over from "L" (low) to "H" (high) when the output voltage of the amplifier 482 drops below the lower partial voltage. The other comparator 486 will change over from L to H when the output voltage of the amplifier 482 exceeds the higher component voltage. The output of the comparator 484 sets the flipflop 472. The output of the comparator 486 resets the flipflop 472.

During the de-energizing phase the flipflop 472 is set. During the proceeding period the comparator 484 was changed over from L to H and set the flipflop when the electromagnet 44 was de-energized. Correspondingly, the signal H is applied to the upper input of the NAND gate 470 in FIG. 3. During the de-energizing phase, the signal at the input 426 is "L". Therefore the output of the NAND gate is H. Correspondingly, voltage is now supplied to the light-emitting diode 468. The light-emitting diode 468 does not emit. Thereby, the photo-transistor 464 is non-conductive. This also causes the switch 406 to be non-conductive, as previously described. Switch 408 is also non-conductive because it is controlled directly, i.e. without further connection, by the control signal at the input terminal 426.

When a control signal H occurs at the input terminal 426, corresponding to the third line of FIG. 4, the switch 408 becomes conductive. Additionally the signal H also occurs at the lower input of the NAND gate 470 in FIG. 4. At this point, both inputs of the NAND gate 470 present condition H. Consequently, the output of the NAND gate 470 changes to condition L. At this point, a voltage is supplied to the light-emitting diode 468. The light-emitting diode 468 emits and thereby causes the emitter-collector junction of the photo-transistor 464 to become conductive. Thereby, also, the switch 406 becomes conductive. At this point, both switches 406 and 408 are conductive. Thereby, the winding 400 is connected to voltage. The current through the winding 400 increases, corresponding to the flank 416, as has been described. Thus, the voltage of the current sensor 474 and the output voltage of the amplifier 482 also increase. When the desired value of the current is achieved, which desired value is determined by the higher partial voltage at the inverting input of the comparator 486, then the comparator switches from L to H. At this point, the flipflop 472 is reset. The output signal of the flipflop becomes L. Thereby, both inputs of the NAND gate 470 no longer present condition H. The output of the NAND gate 470 becomes H. The light-emitting diode 468 is extinguished. Thereby the photo-transistor 464 becomes non-conductive and the switch 406 becomes non-conductive. Hereby the decrease 418 of the current is effected as described with reference to FIG. 4, until the current drops below the lower partial voltage at the non-inverting input of the comparator 484. This effects again the setting of the flipflop and renders the switch 406 conductive.

The mean current through the winding 400 of the electromagnet 44 is maintained between the values determined by the higher and lower partial voltages.

When the signal at the input terminal 426 at the point 498 FIG. 4 drops off to L, that means the measuring time for the background absorption is terminated, on one hand the switch 408 changes to the non-conductive state and, on the other hand, the signal at the lower input of the NAND gate 470 in FIG. 3 changes to state L. This causes a signal H at the output of the NAND gate 470 and extinction of the light-emitting diode 468. Therefore, also, the switch 406 becomes non-conductive. At this point, the effect described occurs so that the current of the induced voltage charges the capacitor 424 through the diodes 402 and 404.

Thus, the arrangement described permits the application of the magnetic field to the furnace for a relatively long measuring time and measurement by means of the Zeeman effect. Thus the measurement of the background absorption by the Zeeman effect is not limited to a short time period around the maxima of the mains voltage as in the prior art instruments. The alternating frequency by which the magnetic field is switched on and off is also not tied to the mains frequency. The influences of mains variations are eliminated by repeated control of the supply voltage and the magnet current.

Figure 5:
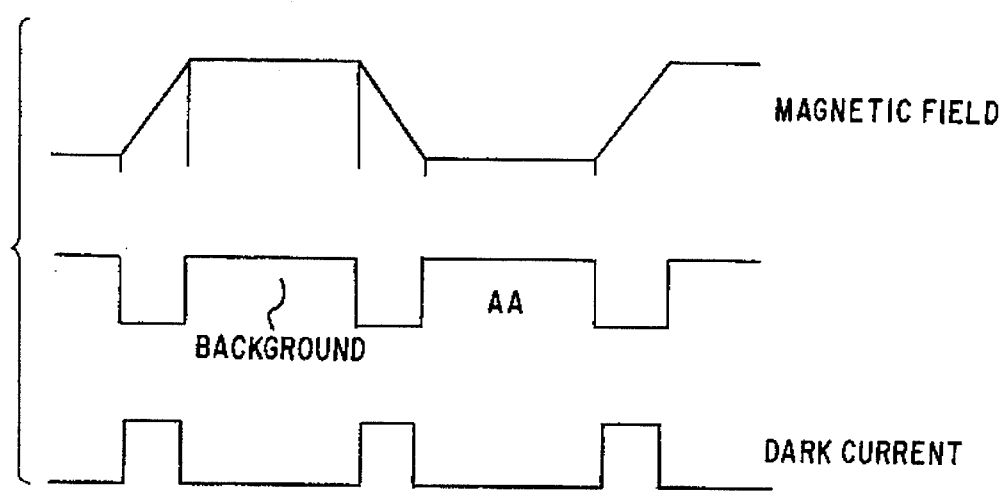
FIG. 5 shows the waveform of the current in the winding of the electromagnet, the switch-on phases of the line-emitting light source and the different measuring phases of the signal processing in the atomic absorption spectrometer of FIG. 1.

The flanks of the trapezoidal current waveform are used to determine the "dark current", i.e. that signal which is provided by the detector of the atomic absorption spectrometer when the line emitting light source 16 is switched off. This "dark current" is partially real dark current of the detector but also partially a signal which is caused by emissions of the sample and of the furnace. Consequently, the light source 16 is switched on when the electromagnet 44 is entirely energized, that means the current in the winding 400 corresponds to the desired value, or when the current in the winding 400 is zero. In between, during increase and decrease of the current, the light source 16 is switched off. When the electromagnet 44 is energized, the background absorption is determined. A measurement of the background absorption plus atomic absorption is made, when the electromagnet 44 is de-energized. When the light source 16 is switched off, the dark current is determined in the area of the flanks. The circuit described allows a mode of operation in which nearly the same time intervals are available for background measurement, atomic absorption measurement and dark current measurement during each measuring cycle. This is illustrated in FIG. 5.

Figure 6:
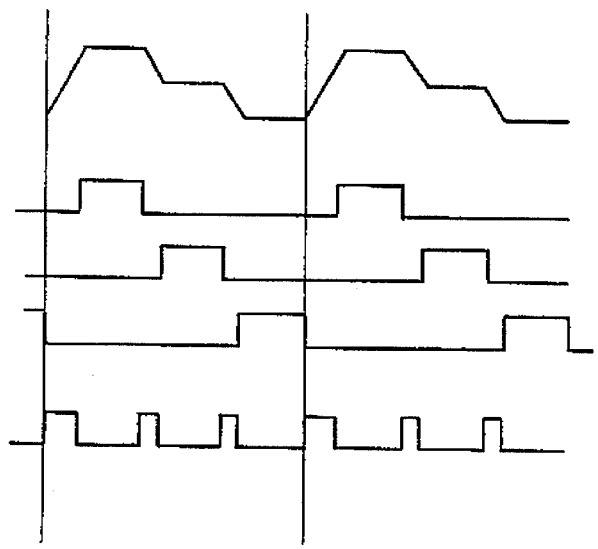
FIG. 6 shows the waveform of the current and the different measuring phases in "three-field-operation" for enlarging the dynamic measuring range of the atomic absorption spectrometer.

FIG. 6 illustrates a further mode of operation which is permitted by the arrangement described. It has been found that the dependence of the logarithmized absorption on the amount of the element looked for in the sample may be highly non-linear in an atomic absorption spectrometer with the Zeeman atomic absorption spectroscopy ("Applied Spectroscopy" vol. 38 (1984), 141–148). A linearizing can be achieved in that the background absorption is measured with two different field intensities of the magnetic field. Thereby the measuring range can be enlarged.

The arrangement described permits a waveform of the current in the winding 400 of the electromagnet 44 as illustrated in FIG. 6 by the input of corresponding desired values to the input terminal 488. Then a measurement is conducted with a strong magnetic field, a measurement is conducted with a weak magnetic field and a measurement is conducted with the magnetic field switched off corresponding to the second, third and fourth line of FIG. 6. The dark current is again measured in the area of the flanks.

We claim:

1. An atomic absorption spectrometer in which background absorption is compensated by means of a magnetic field causing a periodic line shift due to the Zeeman effect, containing
   (a) a line emitting light source (16) which emits a measuring light beam containing the line spectrum of an element to be detected,
   (b) an atomizing device (42) for atomizing a sample to be investigated and for forming an atom cloud in which the atoms of the element, which atoms are contained in the sample, are present in an atomic state,
   (c) an optical system (20,22) by means of which the measuring light beam (16) can be passed through the atom cloud of the atomizing device (42),
   (d) an electromagnet (44) which can be periodically energized and deenergized, for producing the Zeeman effect at the location of the atomizing device,
   wherein the improvement comprises:
   (e) a converter circuit (216,218,220) for providing a d.c. voltage to a capacitor (424),
   (f) a winding (400) of the electromagnet (44) located in a diagonal of a bridge circuit which
      is supplied with the d.c. voltage of said converter circuit (216,218,220), and
      comprises a respective diode (402,404) in diametrically opposite branches and a respective first and second controlled switch (408,406) in the other two branches,
   (g) the first one of the controlled switches (408) is periodically maintained conductive by control means (414) at the frequency of energizing and deenergizing the electromagnet (44), during an active time period encompassing the build-up and maintenance of the magnetic field, said first controlled switch being non-conductive during the remaining time,
   (h) the second one of the controlled switches (406) is controlled by means of a two-step current controller (484,486,472,468) for regulating a predetermined current flowing through the winding (400) of the electromagnet (44) during said active time period of the first controlled switch (408), said second controlled switch likewise being non-conductive during the remaining time so that there results an essentially trapezoidal current waveform, and
   (i) the winding (400) of the electromagnet (44) is connected in series with the diodes (402,404) to the capacitor (424) of the converter circuit (216,218,220) in the non-conductive state of both of the controlled switches (406,408).

2. An atomic absorption spectrometer according to claim 1, further comprising
   (a) lamp control means for switching the line emitting light source (16) of the atomic absorption spectrometer on when the electromagnet (44) is de-energized and when the electromagnet (44) is fully energized, said light source being switched off during the ascending and descending flanks of the current waveform in the winding (400) of the electromagnet (44) and
   (b) means for determining dark current and emission radiation of the atomic absorption spectrometer during the switched-off periods of the light source.

3. An atomic absorption spectrometer according to claim 1 or claim 2, wherein a set point of the two-step current controller means is variable in at least two steps during the active time period of the first controlled switch (408).

* * * * *